United States Patent
Michopoulos et al.

(10) Patent No.: US 9,046,353 B2
(45) Date of Patent: Jun. 2, 2015

(54) SYSTEM AND METHOD FOR REMOTE FULL FIELD THREE-DIMENSIONAL DISPLACEMENT AND STRAIN MEASUREMENTS

(75) Inventors: John G. Michopoulos, Washington, DC (US); Athanasios Iliopoulos, Chevy Chase, MD (US); Nikos P. Andrianopoulos, Athens (GR)

(73) Assignee: The United States of America as represented by the Secretary of the Navy, Washington, DC (US)

(*) Notice: Subject to any disclaimer, the term of this patent is extended or adjusted under 35 U.S.C. 154(b) by 462 days.

(21) Appl. No.: 13/565,698

(22) Filed: Aug. 2, 2012

(65) Prior Publication Data

US 2013/0063570 A1    Mar. 14, 2013

Related U.S. Application Data

(60) Provisional application No. 61/514,083, filed on Aug. 2, 2011.

(51) Int. Cl.
*H04N 13/02* (2006.01)
*G01B 11/16* (2006.01)
(Continued)

(52) U.S. Cl.
CPC ............ *G01B 11/165* (2013.01); *G06T 7/0075* (2013.01); *G01N 3/068* (2013.01); *G01N 2203/0017* (2013.01); *G01N 2203/0218* (2013.01); *G01N 2203/0647* (2013.01)

(58) Field of Classification Search
CPC ... H04N 13/02; H04N 17/00; H04N 21/4126; H04N 21/44222; H04N 21/21805; H04N 21/23418; H04N 13/044; H04N 13/0246; H04N 13/0242; A61M 2005/3125; A61M 2005/3142; A61M 5/3135
USPC ............................................... 348/47, 36, 135
IPC ........................................................ H04N 13/02
See application file for complete search history.

(56) References Cited

U.S. PATENT DOCUMENTS

| | | |
|---|---|---|
| 4,432,239 A | 2/1984 | Bykov |
| 4,474,466 A | 10/1984 | McDonach et al. |

(Continued)

FOREIGN PATENT DOCUMENTS

JP    2009264852 A    11/2009

OTHER PUBLICATIONS

International Search Report, PCT/US12/49396, report dated Nov 2, 2012, 8 pages.

(Continued)

*Primary Examiner* — Trang U Tran
(74) *Attorney, Agent, or Firm* — US Naval Research Laboratory; Sally A. Ferrett

(57) ABSTRACT

A method and system for measuring full field deformation characteristics in three dimensions of a body upon which a pattern of visible marks has been applied. The method includes receiving images of the pattern of marks from at least two digital video cameras as the specimen deforms. A computer processor identifies the centroids of each of the two camera images of the body in a first frame, matches the centroids of the marks in the two images, and generates a three-dimensional representation of the centroids based on the two images, and repeats these steps for the images from the two cameras in a subsequent frame. The computer processor calculates the displacement vector between a three dimensional representation of the centroids and the subsequent three dimensional representation of the centroids, and calculates full field displacement and strain fields based on the displacement vector.

17 Claims, 13 Drawing Sheets

(51) Int. Cl.
*G06T 7/00* (2006.01)
*G01N 3/06* (2006.01)

(56) References Cited

U.S. PATENT DOCUMENTS

| | | | |
|---|---|---|---|
| 4,765,189 A | 8/1988 | Preater | |
| 4,872,751 A | 10/1989 | Hercher | |
| 4,967,093 A | 10/1990 | Takemori | |
| 5,166,742 A | 11/1992 | Kobayashi et al. | |
| 5,684,886 A | 11/1997 | Kamada et al. | |
| 6,097,477 A | 8/2000 | Sarrafzadeh-Khoee | |
| 6,563,129 B1 | 5/2003 | Knobel | |
| 6,934,013 B2* | 8/2005 | Vachon et al. | 356/32 |
| 7,344,498 B1 | 3/2008 | Doughty et al. | |
| 7,377,181 B2 | 5/2008 | Christ, Jr. et al. | |
| 2010/0310128 A1 | 12/2010 | Iliopoulos et al. | |
| 2011/0106459 A1 | 5/2011 | Christ, Jr. et al. | |
| 2012/0287248 A1* | 11/2012 | Erdman, III et al. | 348/47 |

OTHER PUBLICATIONS

Extended European Search Report, Application No. 12819237.4-1558/2740075, PCT/US2012049396, dated Dec. 4, 2014, 6 pages.
Andersen, K.; Helsch, R., "Calculation of grating coordinates using correlation filter techniques", Optik, vol. 80, pp. 76-79, (1988).
Andrianopoulos, N. P., "Full-field displacement measurement of a speckle grid by using a mesh-free deformation function", Strain, vol. 42, 265-271, (2006).
Badaliance R. et al., "Effects of Computational Technology on Composite Materials Research: The Case of Dissipated Energy Density", presented at the First Hellenic Conference on Composite Materials Research, Xanthi, Greece, Jul. 2-5, 1997, pp. 1-39.
Belytschko, T.; Lu, Y.Y.; Gu, L., "Element-free Galerkin methods", International Journal of Numerical Methods in Engineering, vol. 3, pp. 229-256, (1994).
Belytschko, T.; Krongauz, Y.; and Organ, D. , "Meshless method: an overview and recent development,"Computer Methods in Applied Mechanics and Engineering, vol. 139, pp. 3-47, 1996.
Bruck, H.A.; McNeil, S.R.; Sutton, M.A.; and Peters, W.H., "Digital image correlation using Newton-Raphson method of partial differential correction", Expt. Mech., vol. 28, pp. 261-267 (1989).
Bruneel, H.C.J., "Intrinsic Errors on Sheet Strain Measurements Based on a Printed Square Grid", J. Manuf. Sci. Eng., vol. 122, pp. 760-765, (2000).
Cheng, P.; Sutton, M.A..; Schreier, H.W.; McNeill, S.R., "Full-field speckle pattern image correlation with BSpline deformation function", Expt. Mech., vol. 42, pp. 344-352, (2002).
Iliopoulos, A.P.; Andrianopoulos, N.P., "An Approach to Analyze Errors Introduced in the Random Grid Strain Measurement Method", Strain, vol. 46, pp. 258-266, Jun. 2010 (published online Nov. 2008).
Iliopoulos, A.P.; Michopoulos, J.G.; Andrianopoulos, N.P., "Performance Sensitivity Analysis of the Mesh-Free Random Grid Method for Whole Field Strain Measurements", Proc. ASME 2008 International Design Engr. Tech. Conferences and Computers and Information in Engineering Conference IDETC/CIE 2008, DETC2008/CIE-49732, Aug. 3-6, 2008, pp. 1-11, (Aug. 2008).
Iliopoulos, A.P.; Michopoulos, J.G., "Effects of Anisotropy on the Performance Sensitivity of the mesh-free Random Grid Method for Whole Field Strain Measurement", Proc. ASME International Design Engr. Tech. Conferences and Computers and Information in Engineering Conference IDETC/CIE 2009, DETC2009/CIE-86962, Aug. 30-Sep. 2, 2009, pp. 1-10.
Lancaster, P.; Salkauskas, K.; "Surfaces Generated by Moving Least Squares Methods", Mathematics of Computation, vol. 37, No. 155, pp. 141-158, (Jul. 1981).
Liu, W.K.; Jun, S.; and Zhang, Y.F., "Reproducing Kernel Particle Methods", International Journal for Numerical Methods in Fluids, vol. 20, pp. 1081-1106, 1995.
Liu, G. R. and Gu, Y. T., "A Local Radial Point Interpolation Method (LRPIM) for Free Vibration Analyses of 2-D Solids", Journal of Sound and Vibration, vol. 246, No. 1, pp. 29-46 (2001).
Liu, G.R. and Gu, Y.T., "A point interpolation method for two-dimensional solids", Int. J. Numer. Meth. Engng., vol. 50, pp. 937-951, (2001).
Michopoulos, J.M.; Hermanson, J.C.; Iliopoulos, A., "Toward a Recursive Hexapod for the Multidimensional Mechanical Testing of Composites", Proceedings of the ASME 2010 International Design Engineering Technical Conferences & Computers and Information in Engineering Conference IDETC/CIE 2010, DETC2010-28699, Aug. 15-18, 2010, pp. 1-9.
Michopoulos, J.M., et al., "Towards the robotic characterization of the constitutive response of composite materials", Composite Structures, vol. 86, pp. 154-164, 2008, (available online Mar. 13, 2008).
Michopoulos, J.G.; Iliopoulos, A., "A computational workbench for remote full field 3D displacement and strain measurements", Proc. of the ASME 2011 International Design Engr. Tech. Conferences & Computers and Information in Engineering Conference IDETC/CIE 2011, DETC2011-47739, pp. 1-10, Aug. 28-31, 2011.
Michopoulos, J.G.; Iliopoulos, A.P.; Furukawa, T., "Accuracy of Inverse Composite Laminate Characterization via the Mesh Free Random Grid Method", Proc. ASME International Design Engr. Tech. Conferences and Computers and Information in Engineering Conference IDETC/CIE 2009, DETC2009/CIE-87096, Aug. 30-Sep. 2, 2009, pp. 1-8.
Michopoulos, J.G.; Iliopoulos, A.P., "A computational workbench for remote full field 2D displacement and strain measurements", Proc. 2009 ASME Int. Design Engr. Technical Conferences and Computers and Information in Engineering Conference IDETC/CIE 2009, DETC2009/CIE-86900, pp. 1-9, Aug. 30-Sep. 2, 2009.
Parks, V. J., "Strain measurements using grids", Opt. Eng., vol. 21, pp. 633-639 (1982).
Peters, W.H.; Ranson, W.F., "Digital imaging techniques in experimental stress analysis", Opt. Eng., vol. 21, pp. 427-432, (1982).
Schreier, H.W.; Sutton, M.A., "Systematic errors in digital image correlation due to undermatched subset shape functions", Expt. Mech., vol. 42, pp. 303-310, (2002).
Sevenhuijsen, P.J., "The Photonical, Pure Grid Method", Optics and Lasers in Engineering, vol. 18, pp. 173-194, (1993).
Sevenhuijsen, P.J., "Two simple methods for deformation demonstration and measurement", Strain, vol. 17, pp. 20-24 (1981).
Sirkis, J.S., "System response to automated grid methods", Opt. Eng., vol. 29, 1485-93, (1990).
Sirkis, J.S.; and Lim, T.J., "Displacement and Strain Measurement with Automated Grid Methods", Experimental Mechanics, V. 31, No. 4, pp. 382-388, Dec. 1991.
Iliopoulos, A. P., Michopoulos, J. G., and Andrianopoulos, N. P., "Performance Analysis of the Mesh-Free Random Grid Method for Full-Field Synthetic Strain Measurements", Strain, vol. 48, pp. 1-15, Feb. 2012, available online Aug. 25, 2010.
Hartley, R. and Zisserman, A., Multiple View Geometry in Computer Vision, 2 ed., Cambridge University Press, cover and pp. 310-313, Apr. 2004.

* cited by examiner

E XX AT TENSILE LOAD = 4207KN

E YY AT TENSILE LOAD = 4207KN

E XY AT TENSILE LOAD = 4207KN

E XX AT TENSILE LOAD = 12018KN

E YY AT TENSILE LOAD = 12018KN

E XY AT TENSILE LOAD = 12018KN

E XX AT TENSILE LOAD = 13639KN

E YY AT TENSILE LOAD = 13639KN

E YY AT TENSILE LOAD = 12018KN

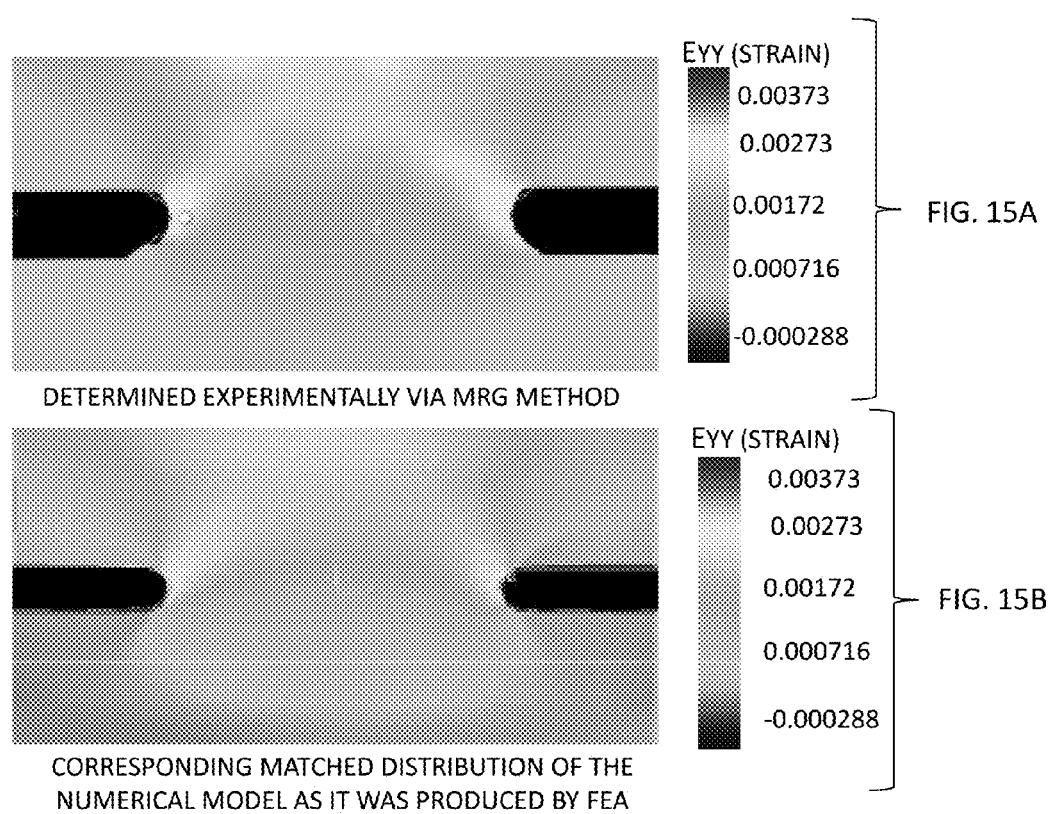

SYSTEM AND METHOD FOR REMOTE FULL FIELD THREE-DIMENSIONAL DISPLACEMENT AND STRAIN MEASUREMENTS

CROSS-REFERENCE TO RELATED APPLICATIONS

This Application is a non-provisional under 35 USC 119(e) of, and claims the benefit of U.S. Provisional Application 61/514,083 filed on Aug. 2, 2011, and claims the benefit of U.S. Provisional Application 61/514,092 filed on Aug. 2, 2011, the entire disclosure of both documents being incorporated herein in their entireties.

BACKGROUND

1. Technical Field

The present invention relates generally to a system for measuring and visualizing the full field of deformation behavior of a body in terms of displacement and strain, and more specifically, to a methodology, algorithms and a corresponding set of tools for the data acquisition, digital image processing, field variable approximation or interpolation and visualization of digital images of a deforming body in three dimensions.

2. Background Technology

Beginning in the 1980's, digital imaging has been used to measure the deformation state of deformable material specimens. These displacement measurement methods have gained significant attention the last two decades, because of the great impact of digital imaging evolution. Modern digital cameras provide a cost effective and highly reliable tool for recording and processing images of an experiment using a personal computer. Experimental mechanics have greatly benefited from those capabilities and some methods have been developed for the determination of displacement and strain fields.

Both pure grid methods and digital image correlation methods have been proposed for providing full-field measurements of displacement and strain.

In pure grid methods, a uniform grid is applied to the surface of a specimen, and the measurement of deformation relies on the motion of the grid. These methods rely on specialized methods for application of the uniform grid. It can be difficult to apply a uniform grid to irregularly shaped bodies, and any inaccuracies in the application of the grid are a major source of errors in the measurement of deformation.

Pure grid methods are described in Sevenhuijsen, P. J., "Two simple methods for deformation demonstration and measurement", Strain, Vol. 17, pp. 20-24 (1981); Parks, V. J., "Strain measurements using grids", Opt. Eng., Vol. 21, pp. 633-639 (1982); Sevenhuijsen, P. J., "Photonics for deformations", Proc 5th Int. Congr. On Expt. Mechanics, SESA, Montreal, (June 1984); and Sevenhuijsen, P. J., "The Photonical, Pure Grid Method", Optics and Lasers in Engineering, Vol. 18, pp. 173-194, (1993).

Digital image correlation methods are described in Peters, W. H., Ranson, W. F., "Digital imaging techniques in experimental stress analysis", Opt. Eng. Vol. 21, pp. 427-432, (1982); Bruck, H. A., McNeil, S. R., Sutton, M. A., and Peters W. H., "Digital image correlation using Newton-Raphson method of partial differential correction", Expt. Mech. Vol. 28, pp. 261-267 (1989); and Cheng, P., Sutton, M. A., Schreier, H. W., McNeill, S. R., "Full-field speckle pattern image correlation with B-Spline deformation function", Expt. Mech., Vol. 42, pp. 344-352, (2002).

The performance of methods based on digital image correlation, which rely on an applied speckle pattern, can be highly sensitive to the application method and on the specimen surface. Schreier, H. W. Sutton, M. A., "Systematic errors in digital image correlation due to undermatched subset shape functions", Expt. Mech., Vol. 42, pp. 303-310, (2002) discusses the sensitivity of the method to very specific qualitative and quantitative characteristics of the speckle pattern.

Additional grid-based methods are described in Sirkis, J. S., "System response to automated grid methods", Opt. Eng., Vol. 29, 1485-93, (1990) and Andersen, K., Helsch, R., "Calculation of grating coordinates using correlation filter techniques", Optik, Vol. 80, pp. 76-79, (1988). U.S. Pat. No. 7,377,181 to Christ, Jr. et al. discloses the use of coded marks.

Bremand, F. and Lagarde, A., "Two methods of large and small strain measurement on a small size area", Proc. SEM Spring Conf. On Expt. Mechanics, Keystone, Colo., USA, pp. 173-176, (1986) discloses a method of applying a Fourier transform of the grid pattern.

Mesh-free methods are described in Andrianopoulos, N. P., "Full-field displacement measurement of a speckle grid by using a mesh-free deformation function", Strain, Vol. 42, 265-271, (2006), in Andrianopoulos, N. P. and Iliopoulos, A. P. "Displacements Measurement in Irregularly Bounded Plates Using Mesh Free Methods", 16th European Conference of Fracture, Alexandroupolis, Greece, Jul. 3-7, 2006.

Two dimensional random-grid mesh-free techniques are disclosed in Andrianopoulos, N. P. and Iliopoulos, A. P., "Strain measurements by a hybrid experimental-numerical method using a mesh-free field function", Honorary Volume for Professor P. S. Theocaris, Armenian Academy of Sciences, 31-41, (2005) and in Iliopoulos, A. P., Andrianopoulos, N. P., "An Approach to Analyze Errors Introduced in the Random Grid Strain Measurement Method", Strain, Vol. 46, pp. 258-266, June 2010 (published online November 2008), and in copending patent application Ser. No. 12/793,594 to Michopoulos et al., published as U.S. Patent Publication No. 20100310128, the entire disclosure of which is incorporated herein by reference.

Early development of six degree-of-freedom (DoF) mechatronic technology is described in J. G. Michopoulos, J. C. Hermanson, A. Iliopoulos, "Toward a Recursive Hexapod for the Multidimensional Mechanical Testing of Composites, Proc. ASME International Design Engineering Technical Conferences & Computers and Information in Engineering Conference IDETC/CIE 2010, held 15-18 Aug. 2010. Three dimensional hexapod materials testing machines developed by the Naval Research Laboratory and the USDA Forest Products Laboratory are also described in J. G. Michopoulos, J. C. Hermanson, and T. Furukawa, "Towards the robotic characterization of the constitutive response of composite materials", Composite Structures, Vol. 86, pp. 154-164, 2008. A recent recursive hexapod materials testing machine is described in U.S. patent application Ser. No. 13/400,170, filed on Aug. 2, 2012, and in J. Michopoulos et al., "Towards a Recursive Hexapod for the Multidimensional Mechanical Testing of Composites", ASME 2010 Design Engineering Technical Conferences and Computers and Information in Engineering Conference (IDETC/CIE2010). The entire disclosure of each of these documents is incorporated herein in its entirety.

BRIEF SUMMARY

A computer-implemented method for measuring full field deformation characteristics in three dimensions of a deformable body upon which a visible dot pattern has been applied, the method comprising: (a) receiving from two imaging devices, two sequences of images of the dot pattern before and after deformation of the body, the sequence of images including a first frame and a second frame separated in time; (b) for both images in the first frame, identifying the centroids of the dots with a computer processor, matching the centroids of the dots in an image from one imaging device to the centroids of the dots in a corresponding image from the other imaging device, and generating a three dimensional image of the centroids of the pattern of dots from the two images; (c) repeat steps (b) for both images in the second frame; (d) matching the centroids in the three dimensional image of the centroids in the first frame to the centroids in the three dimensional image of the centroids in the second frame; (e) calculating the displacement vector of the centroids between the first frame and the second frame; and (f) calculating full field displacement in three dimensions based on the displacement vector of the centroids.

The method can also include calculating a full field strain tensor based on the displacement vector of the characteristic points. The full field displacement and strain is calculated using a mesh free approximation.

The step of receiving two sequences of images can include digitally photographing the side of the deformable body during deformation with two digital video cameras. The method can also include generating the dot pattern with a random number generator.

The step of identifying the characteristic points of the dots includes light integration of the image to find the centroid of each dot. The method can also include eliminating irregular objects from both images in plurality of frames in the sequences of images. This can include eliminating objects with a dot intensity below a threshold value, objects with a pixel area outside a predetermined range, or objects with an out-of-range aspect ratio, an out-of-range moment of inertia, an out-of-range major axes direction, or an out-of-range compactness ratio.

The method can also include receiving performance characteristics from a user, and selecting mesh free approximation parameters based on the performance characteristics. The method can also include displaying and storing the acquired images, user input, and calculated displacement and strain component, wherein said displacement and strain components are graphically shown using a color scale. The method can also include displaying a color image of displacement, elongation, or strain versus time or image frames.

Another aspect of the invention is directed to an apparatus for measuring full field deformation characteristics of a body having a pattern of optically distinct marks disposed on a surface of the specimen. The apparatus includes two digital video cameras for acquiring two sequence of images of the pattern of marks before and after deformation of the specimen, and a computer processor having programmed instructions thereon for identifying the centroids of each image in the sequences of images, matching the centroids between the two images in a frame, generating a three-dimensional representation of the centroids based on the two images, calculating the displacement vector of the centroids of a pair of images and a later pair of images, and calculating full field displacement and strain fields based on the displacement vector of the centroids using a mesh-free approximation.

The apparatus processor can also include instructions for calculating a full field strain tensor based on the displacement vector of the centroids, with the full field displacement and strain being calculated using a mesh free approximation. The processor can have further instructions for identifying the characteristic points of the dots by light integration of the image to find the centroid of each dot. The processor can have further instructions for eliminating irregular objects from both images in plurality of frames in the sequences of images based on objects having a gray-scale intensity below a threshold value of intensity, a pixel area outside a predetermined range, an out-of-range aspect ratio, an out-of-range moment of inertia, an out-of-range major axes direction, or an out-of-range compactness ratio. The apparatus processor can have instructions for a graphical user interface for receiving performance characteristics from a user, and selecting mesh free approximation parameters based on the performance characteristics. The apparatus can also include a display connected to the processor, with the processor having further instructions for displaying and storing the acquired images, user input, and calculated displacement and strain component, wherein said three dimensional displacement and strain components are graphically shown using a color scale.

BRIEF DESCRIPTION OF THE DRAWINGS

FIGS. 15A and 15B show the $\epsilon_{yy}$ results for the material test determined using the ReMDiS-3D software and the results of finite-element-analysis numerical model of the same specimen, respectively.

DETAILED DESCRIPTION OF EMBODIMENTS OF THE INVENTION

The following description discloses a computational workbench infrastructure that implements a Meshless Random Grid (MRG) method for the remote (non-contact) measurement of displacement and strain fields in three dimensional space. The method is applicable to structures bounded by flat surfaces that deform under various mechanical and generalized loading conditions in and out of plane.

The workbench can provide efficient and inexpensive displacement and strain field determination as a critical element of a data-driven material characterization methodology via mechatronically automated robotic testing machines, using a mesh-free (or mesh-less), random grid (MRG) method that takes advantage of the properties of mesh-free approximations to represent the displacement and strain fields. These properties include the ability to represent high order continuity of the underlying field, the ability to handle irregular domains and nodal distributions of general nature (deterministic and/or stochastic). The procedural basis of the MRG method follows the following four steps to accomplish the measurement of strain:

1. A specimen is marked with a random distribution of spots with inverse chromatic and/or intensity value of that to the main color of the specimen itself.
2. Digital images of the un-deformed and deformed specimen are acquired and a simple labeling algorithm is used to identify the centers of the spots (centroids) on each image.
3. A point matching algorithm identifies the correspondence between centroids of the spots in the two images and calculates the respective displacement.
4. The obtained values of the displacement of the centroids are used to calculate the full-field values of displacement and strain through mesh-free interpolation functions.

The random distribution of points and Mesh-Free surface approximation is extended from two to three dimensions, by using principles of computer vision techniques. For three dimensions, the mesh-less random grid system operates as follows.

Figure 1:
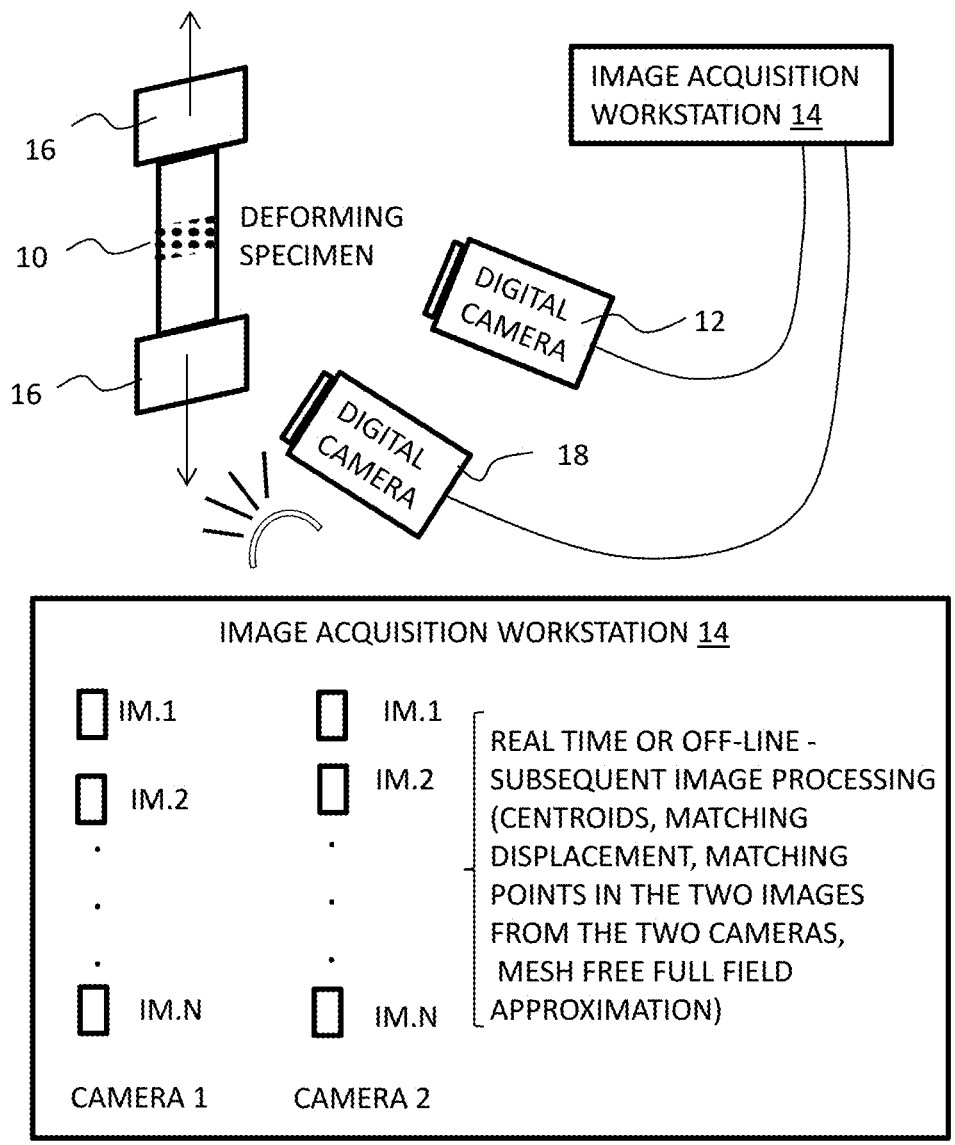
FIG. 1 shows the system for measuring deformation of a surface in three dimensions, including two video cameras, a materials testing machine and specimen, and an image acquisition workstation.
Figures 2A, 2B:
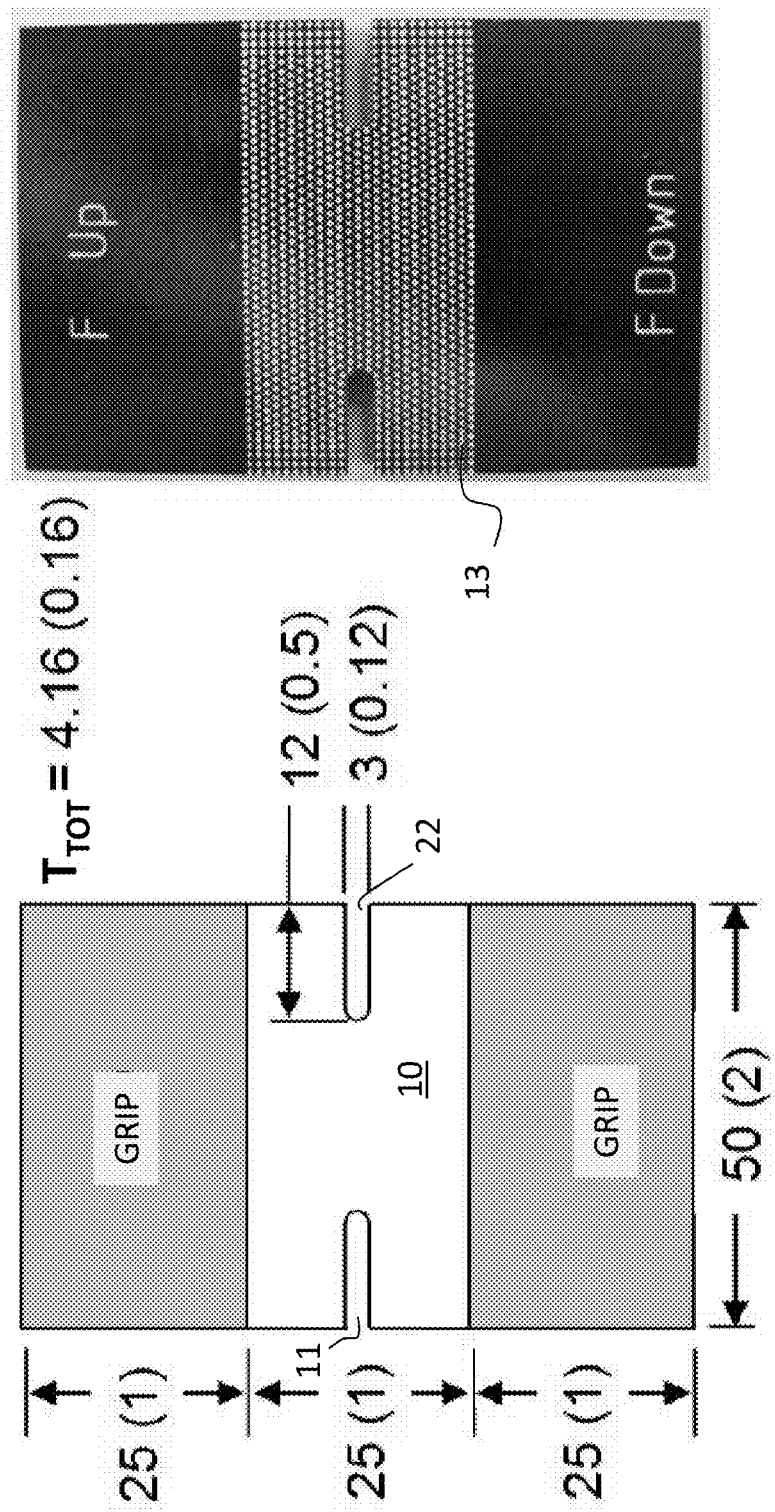
FIGS. 2A and 2B illustrates the face of a typical test specimen.

FIG. 1 illustrates the basic instrumentation required for measuring deformation of a surface in three dimensions, including two video cameras 12 and 18 capturing images of a deforming specimen, a materials testing machine 16, and an image acquisition workstation 14. FIGS. 2A and 2B illustrates the face of a test specimen 10. The specimen 10 is marked with a random distribution of spots colored so that they can be visually distinguishable from the specimen's natural color.

It is noted that the specimen 10 shown herein is a planar specimen with a flat surface on which the spots are applied. This specimen is shown for illustration purposes only. The three dimensional ReMDiS system described herein can be applied to materials having a variety of shapes. The marks can be applied to an initially planar surface, with the analysis software being capable of determining the full three dimensional displacement and strain field resulting from deformation of the specimen.

Figure 3:
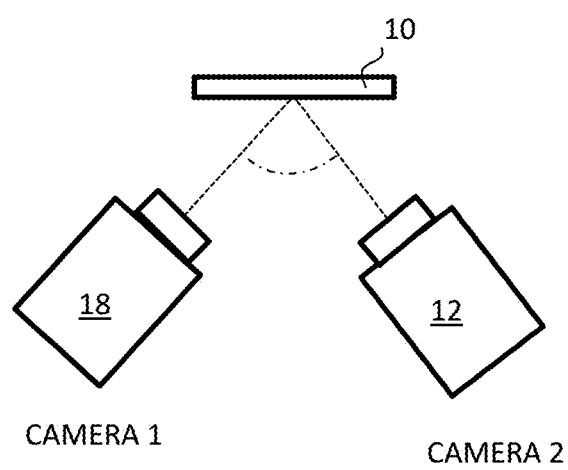
FIG. 3 illustrates a top view of two digital video cameras 12 and 18 positioned to capture the images of the deforming specimen 10 for displacement and strain analysis in accordance with an embodiment of the invention.

FIG. 3 illustrates a top view of two digital video cameras 12 and 18 positioned to capture the images of the deforming specimen 10, each of the video cameras forming a different angle with respect to surface of the specimen. The specimen is exposed to mechanical loading that can result in both in-plane and out of plane deformations. The image acquisition workstation processor integrates computer vision methods and the MRG method principles, to calculate the displacement and the strain field over the surface of the specimen for the various subsequent captured frames.

Note that both the front and the back face of the specimen 10 can be marked with a random grid pattern. The back of the specimen can be imaged with a second pair of cameras (not shown) that face the back of the specimen.

Figure 4:
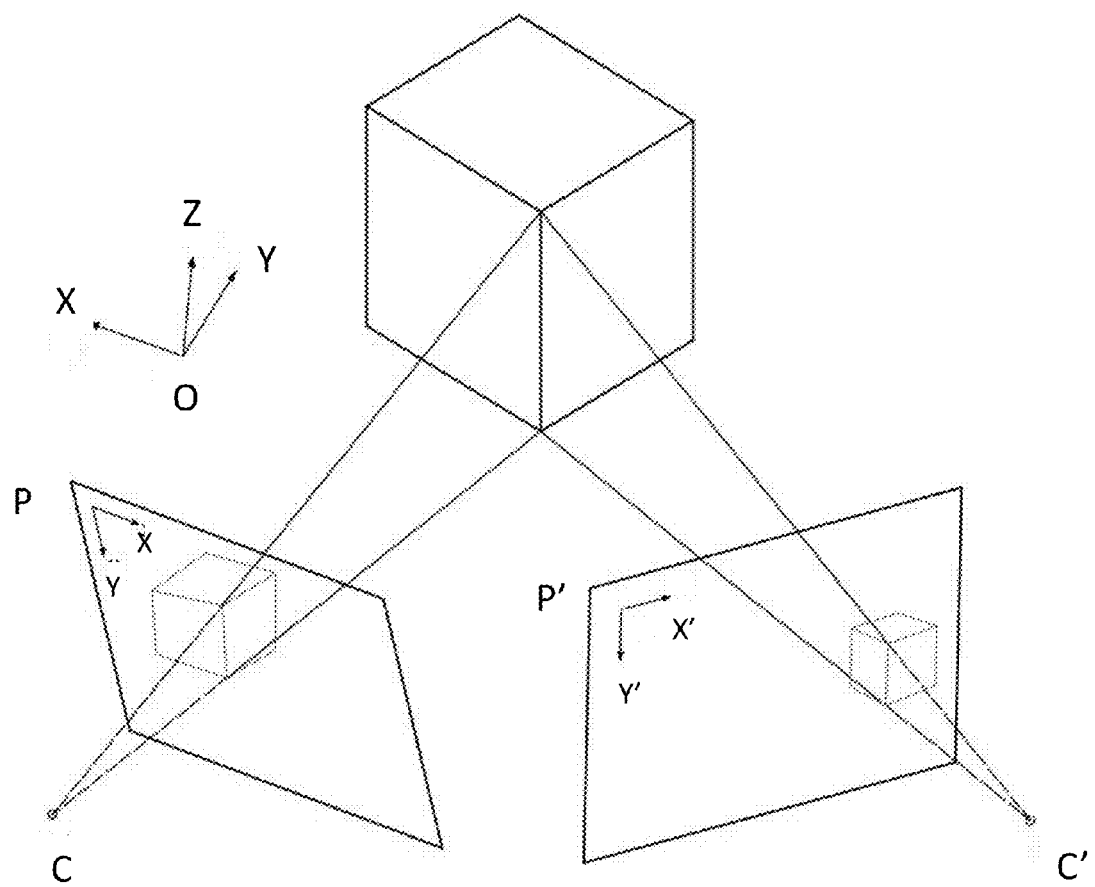
FIG. 4 shows the image of an object projected on the camera planes of a pair of stereo cameras for three-dimensional displacement measurements.

In 2D case, camera positioning and projective characteristics do not matter as long as its image acquisition plane is kept parallel to the deformation plane, because strain is a dimensionless quantity, and therefore invariant to scaling. In contrast, when 3D measurements are desired, the projective characteristics of conventional cameras are essential in determining the 3D coordinates of interest points. As shown in FIG. 4, the image of an object is projected on the camera planes of a pair of stereo cameras 12 and 18. In simplest case (which is enough for the description of many real cameras), this projection can be described by the "pinhole" camera model and expressed by the equation:

$$x = PX \tag{1}$$

where $x = \{x, y, 1\}^T$ is the point on the plane of the camera in homogeneous coordinates, P is a 3×4 projection matrix, also known as the camera matrix and $X = \{X, Y, Z, 1\}^T$ is the vector representing a point in 3D in homogeneous coordinates.

By identifying those projection matrices (through a calibrating process for the cameras), the coordinates of points that are matched between the images captured by the two cameras through triangulation can be determined. If the points are known to lie on a plane, the rigid transformation that maps them on this plane is easily found. However, this procedure can yield point "clouds" for a sequence of frames due to movement of the points when the specimen is deformed. A matching algorithm is needed in order to identify each of those points through the subsequent frames and calculate the corresponding displacements. Those displacements of the randomly distributed points can then be exploited by mesh-free approximation functions, to determine their value over the entire surface:

$$\left. \begin{array}{l} u_x^h(x) = \sum_{i=1}^{N} \varphi_i(x) u_{ix} \\ u_y^h(x) = \sum_{i=1}^{N} \varphi_i(x) u_{iy} \\ u_z^h(x) = \sum_{i=1}^{N} \varphi_i(x) u_{iz} \end{array} \right\} \tag{2}$$

where $u_{ix}$, $u_{iy}$ and $u_{iz}$ are the displacement components of known points (i=1, ..., N) around a region of the point x, the displacement needs to be determined, and $\varphi_i$ are values of a shape function constructed as described in Andrianopoulos, N. P., and Iliopoulos, A. P., "Displacements measurement in irregularly bounded plates using mesh free methods", Proc. 16th European Conference of Fracture, Alexandroupolis, Greece, July 3-7; Andrianopoulos, N. P., and Iliopoulos, A. P., "Strain measurements by a hybrid experimental-numerical method using a mesh-free field function", Honorary Volume for Professor P. S. Theocaris, Armenian Academy of Sciences, pp. 31-41, 2006; and Andrianopoulos, N. P., "Full-Field displacement measurement of a speckle grid by using a Mesh-Free deformation deformation function", Strain, 42(4), pp. 265-271, 2006.

To determine the corresponding strain field distributions, it can be preferable to numerically calculate the derivative of the displacements in equation 2, as this can resolve many algorithmic issues with irregular boundaries. The approximation of the strain tensor is given by:

$$E_{kl} = \frac{1}{2}\left(\frac{\partial u_k}{\partial u_l} + \frac{\partial u_l}{\partial u_k} + \frac{\partial u_m}{\partial u_k}\frac{\partial u_m}{\partial u_l}\right) \quad (3)$$

For a plane (xy) in space (xyz), the indices k, l, and m of equation 3 take the values k,l=x,y and m=x,y,z. In small displacement situations the last multiplicative term of equation 3 and the last equation in equation 2 can be neglected.

The three dimensional method includes the following actions:

1. Mark specimens with a random distribution of spots with inverse chromatic and/or intensity value of that to the main color of the specimen itself;
2. determine the camera matrices (prior to conducting an actual experiment).
3. acquire digital images of un-deformed and deformed specimen during a test using two cameras or other imaging devices, and use a labeling algorithm to identify the centers of the spots (centroids) on each image.
4. Determine points in 3D for every frame corresponding to a different deformation field by
   (a) Determining points in stereoscopic images.
   (b) Point matching between the left and right stereoscopic images using a point matching algorithm.
   (c) Using camera matrices and matched points, determine the points in 3D.
5. Calculation of displacement and strain, by
   (a) Point matching between subsequent frames.
   (b) Determination of displacements for all points.
   (c) Determination of normal vector of the undeformed plane.
   (d) Rotation of the plane to coincide with the global reference system.
   (e) Mesh-Free approximation of the displacement field.
   (f) Determination of the strain tensor from the displacement field, with the obtained values of displacement of centroids being used to calculate the full-field values of displacement and strain through mesh-free interpolation functions.

The workbench for calculating full field planar strains (called "ReMDiS-3D" for Remote Measurement of Displacement and Strain in three dimensions) accomplishes Full Field calculation of planar strains and displacements from sets of images of the randomly marked deforming specimens. The ReMDiS-3D software that accomplishes this method can preferably operate on any of the three major Operating Systems (Linux, Mac OS X and Windows) and can take advantage of multiple core central processing units to increase overall speed.

The main visualization element of the system is a central 3D widget in the graphical user interface display that plots all the features of interest. The objects exist in the real 3D coordinates, with the images being placed at the positions the CCD array is calculated to be relative to the global coordinate system defined by the calibration object, so the specimen is rendered at global position relative to the calibrated object.

The application works on images of in a format that encapsulates a stereo image, formed by the left and right images captured by the video cameras 12 and 13. The ReMDiS-3D software operating on the image acquisition workstation processor 14 loads each pair in a sequence, identifies through a segmentation algorithm the points of interest in each of the two images in the corresponding frame, and matches the points of interest between the two images. The points are also referred herein as either nodes, when used in the context of the mesh-free approximation, or as centroids when referred in the context of image processing.

A labeling module or algorithm identifies an invariant point that is characteristic of each dot in a first specimen image and a later specimen image. The characteristic points can be centroids of regions in close proximity that share light intensity and/or color characteristics. The characteristic point can be any geometric point that can be proved to be mostly invariable related to the overall position of the dot. Those invariable points may be the light intensity centroids of connected components (dots), the two edges of a line, or characteristic points of a pattern such as the center of a circle or the two foci of an ellipse. Each image can be first thresholded to a black and white representation. For example, pixels with a color or grayscale value below a specified intensity threshold are saved as black and pixels with a color or grayscale value above the specified threshold are saved as white pixels. From this procedure, a new image is generated with its pixels being either black or white. Only those pixels in the original image which have been thresholded to black in the black and white image will be processed by the point matching and subsequent steps of the method. The threshold can be adjusted based on the images (e.g., if the test is set up with insufficient light or other adverse conditions) to ensure an effective threshold is used. The threshold can be stored as a preset value in the computer program. The centroid of each mark can be found by integrating the light intensity (e.g., pixel color or grey value) over the area of each dot in the filtered color or grayscale images. Once found, the centroids of the dots in the images can now be considered "Nodes" of a field function for the following point matching steps.

After a reliable threshold value is chosen, the labeling module's algorithm identifies the connected components in the color or grayscale images. In some cases, this procedure can identify irregular dots that are unlikely to be the applied dots. For example, the edge of the image may include dark irregular areas that are not dots. To avoid errors that could occur if these irregular components are processed as dots, the computer program includes a segmentation algorithm for distinguishing objects having a pixel area that is too large or too small to be one of the dots. The computer program includes an upper and a lower area cut-off limit, with the applied dots area being between these upper and lower limits. If the object has a pixel area greater than the upper area cut-off criterion or smaller than the lower cut-off limit, the object is considered an outlier and will not be considered in subsequent steps. Other features can be used to as cut-off criteria, depending on the type of applied marking. Examples include, but are not limited to, compactness ratio, direction of major axis, moment of inertia, and aspect ratio.

After the centroids are matched, the centroids are used to generate the reconstructed geometry of that frame. The geometry is reconstructed in three dimensions using the principles of computer vision and results in a full 3D model of the surface represented by the centroids for that image frame.

ReMDiS-3D also matches the centroids (points) in the frame's 3D image, with the points in the previous frame, and calculates the displacement (how much the centroid has been displaced) during the step between the earlier and later frame. The displacements are then used in a mesh free approximation technique to calculate the displacements and strains for each marker centroid in the random pattern area on the specimen.

In an exemplary embodiment, the matching or linking of the 3D points between two or more sequential images, is based on a naïve matching algorithm. The point matching algorithm can be accomplished by a supervised or un-supervised pattern matching procedure. The matching procedure can be based on, but is not limited to, one or more of the following measures: topological location of points, light intensity measures (maximum, minimum, mean, total, etc.), pixel area coverage of a component, orientation of components, the ratio of the component's width to its height, the moment of inertia on one or two axis, or the ratio of moments of inertia, or the principal axis orientation) or other geometric characteristics.

The user's tasks can include the following:

1. Load the camera parameters, or "camera calibration", into the graphical user interface. This can be also done using a common project template file for a series of experiments for cameras known to retain their position and lens characteristics.

2. Load the first image pair in the set of images.

3. Adjust the threshold and the area limit filters, until the segmentation algorithm detects the desired features.

4. Optionally, manually remove redundant or outlier features of the images, until only the centroids of interest remain.

5. Initiate the initial 3D reconstruction algorithm, by choosing a point on one image that matches a point on the other image.

6. Choose the Mesh-Free parameters and initialize the Mesh Free shape functions.

7. Start the main mesh free random grid method loop. While ReMDiS-3D is running on the computer processor or processors, the appropriate plots can be chosen for viewing in real time on an attached computer display screen.

8. After the analysis is complete, previous frames can be chosen for further inspection, the results can be exported, or sequences of images captured for illustrations or videos.

Figure 5:
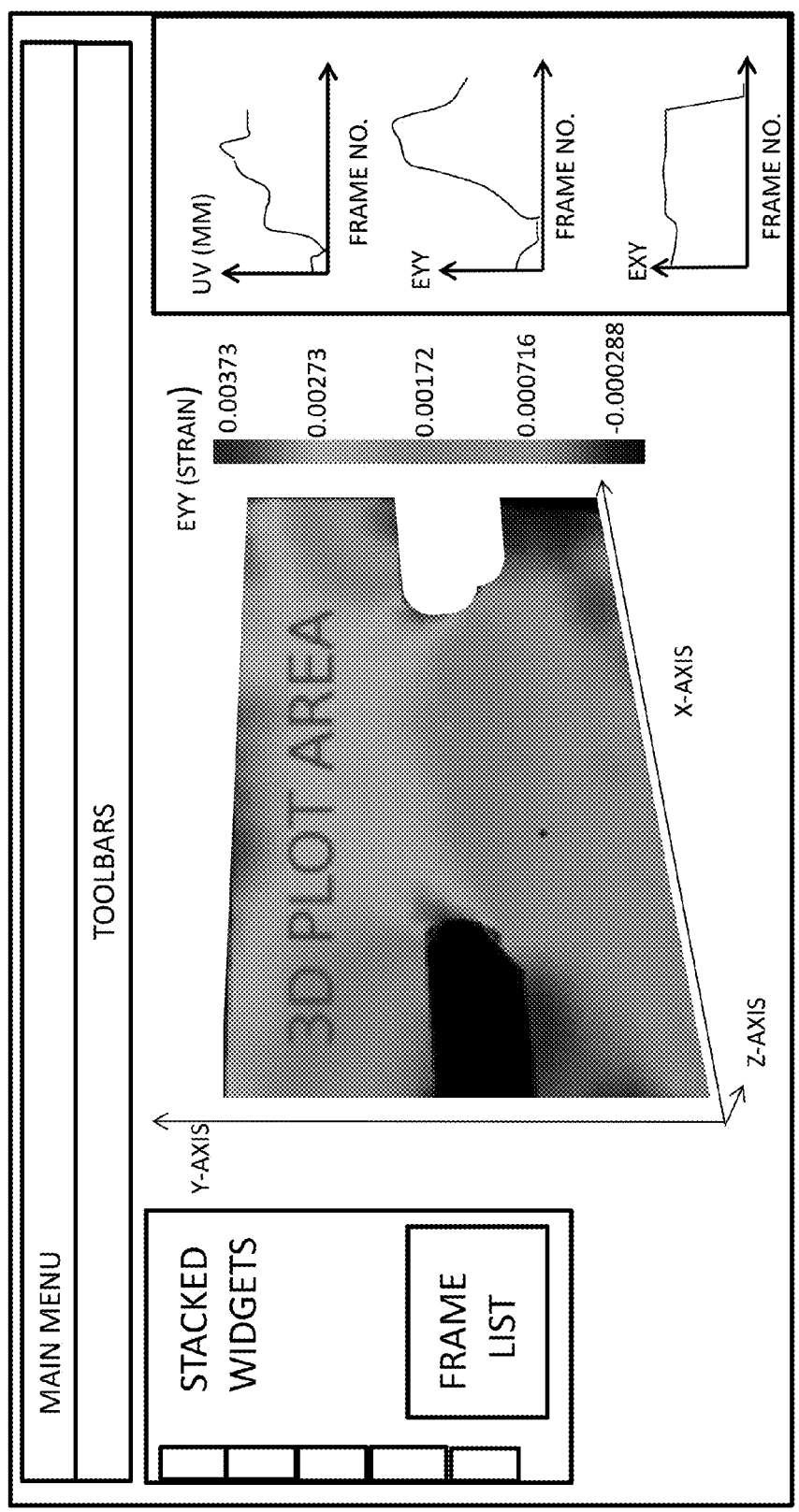
FIG. 5 illustrates the graphical user interface for the ReMDiS-3D software running on the image acquisition workstation processor in accordance with an embodiment of the invention.

FIG. 5 illustrates the graphical user interface for the ReMDiS-3D software running on the image acquisition workstation processor. The graphical user interface screen includes a Main Menu and the Toolbar, the Stacked Widgets Tab, the Frame List, the 3D Plot Area and the 2D Plot Areas. The user can control the size of each of those widgets by dragging the boundaries between them.

The main menu and the toolbar contain most of the action commands in ReMDiS-3D. Those include a file menu, a view menu, the pre-processing menu, and the analysis menu. The file menu allows a new project to be created, saved or retrieved from the hard disk. From this menu, a ReMDiS-3D script file can be executed, that is basically a mini-language that can be used to serially invoke commands saved in a text file. The view menu is used to manipulate the camera of the 3D window, and orient it relative to the global coordinate system. The view menu also contains commands that can be used to toggle the visibility of the coordinate system axis, the identified centroids of the MRG method dots as glyphs in the 3D window, the labels of identified centroids of the MRG method dots, the images of the left and right cameras, the 3D reconstructed surface of the specimen, the full field measurement contours surface. The pre-processing menu is used for capturing the base frame from the appropriate device (camera or data file of previous images), removing outlier points falsely detected by the labeling procedure, initializing the computer vision setup, and manually capturing subsequent frames. The analysis menu is used to initialize and start the automated MRG method analysis of frames captured from the device, export results, images or sequences of images.

The stacked widget tabs shown in FIG. 5 control most of the user inputs for the system. In those widgets most of the options of the application are displayed and can be manipulated. The tabs can be set up and stored in the ReMDiS-3D project files. The widget tabs include Calibration, Device, Segmentation, Geometry, MRG method and Plots.

Figure 6:
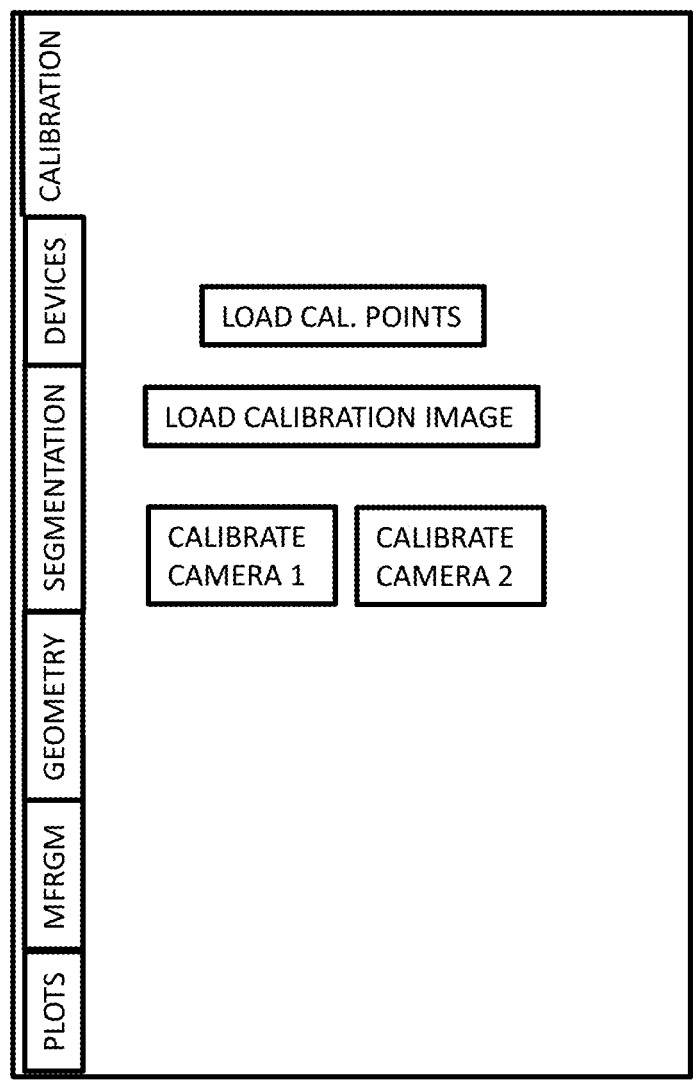
FIG. 6 shows the calibration widget portion of the graphical user interface.
Figure 7A:
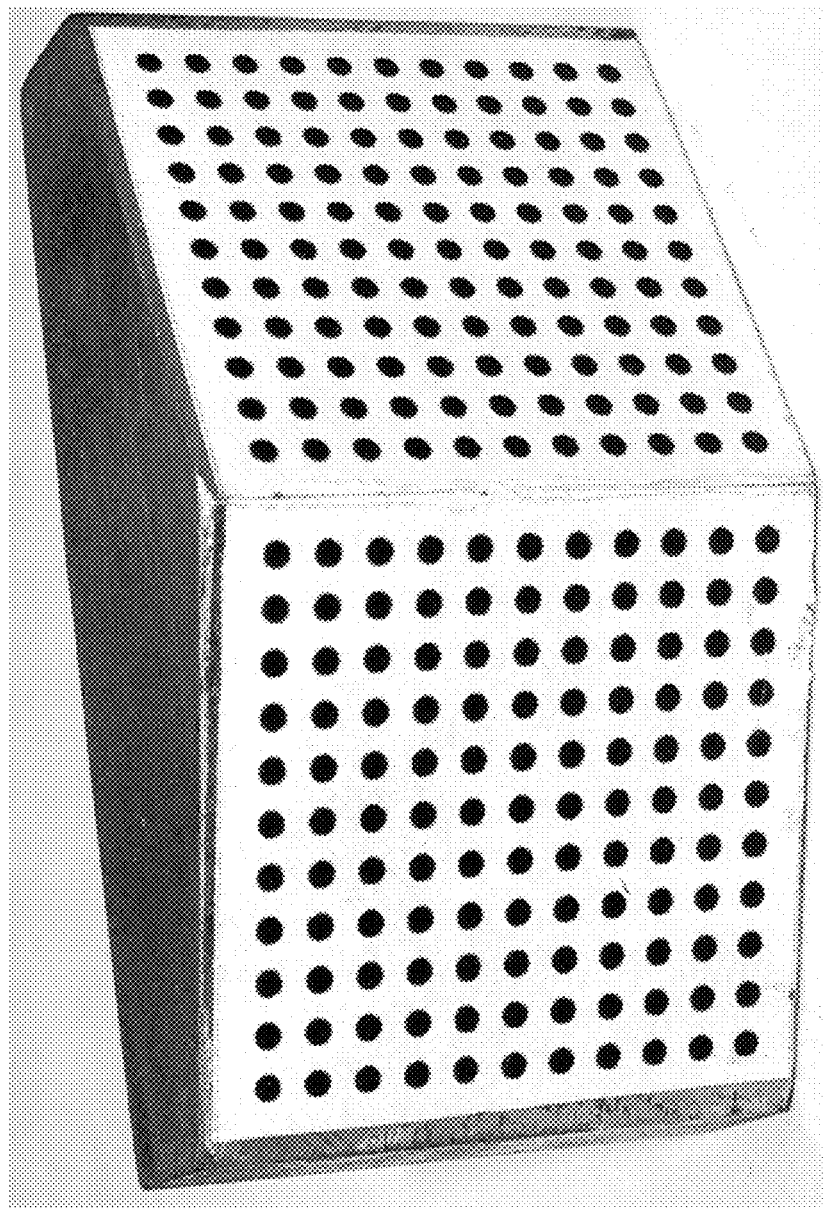
FIG. 7A shows a calibration object.
Figure 7B:
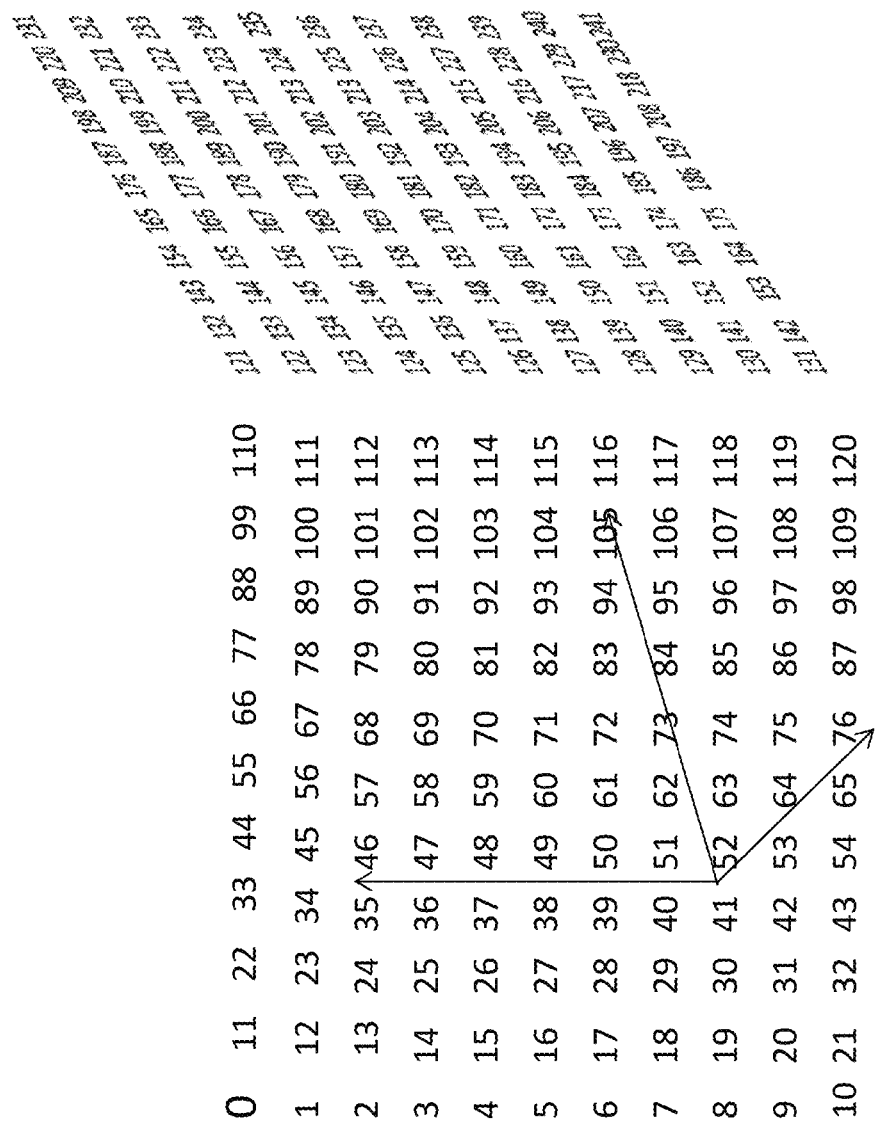
FIG. 7B shows the calibration points in three dimensions.

FIG. 6 shows the calibration widget portion of the graphical user interface. FIG. 7A shows a calibration object, and FIG. 7A shows the calibration points in three dimensions. In the calibration tab, the actions required for calibrating a pair of cameras can be executed. Typically the user loads a list of calibration points from an appropriately formatted text file and a calibration stereo image. The calibration points loaded into ReMDiS-3D can be seen in FIG. 7B, based on the example calibration object shown in 7A. By choosing the appropriate threshold values in the Segmentation tab, ReMDiS-3D can detect the appropriate features used for the calibration. If redundant features are still present, they can be removed using a pre-processing option for removing the redundant features, with the function "Remove Points".

After the points are identified the cameras can be calibrated using the push-buttons on the graphical user interface to select one point in each image corresponding to a known point identification in the 3D calibration point list.

Figure 8:
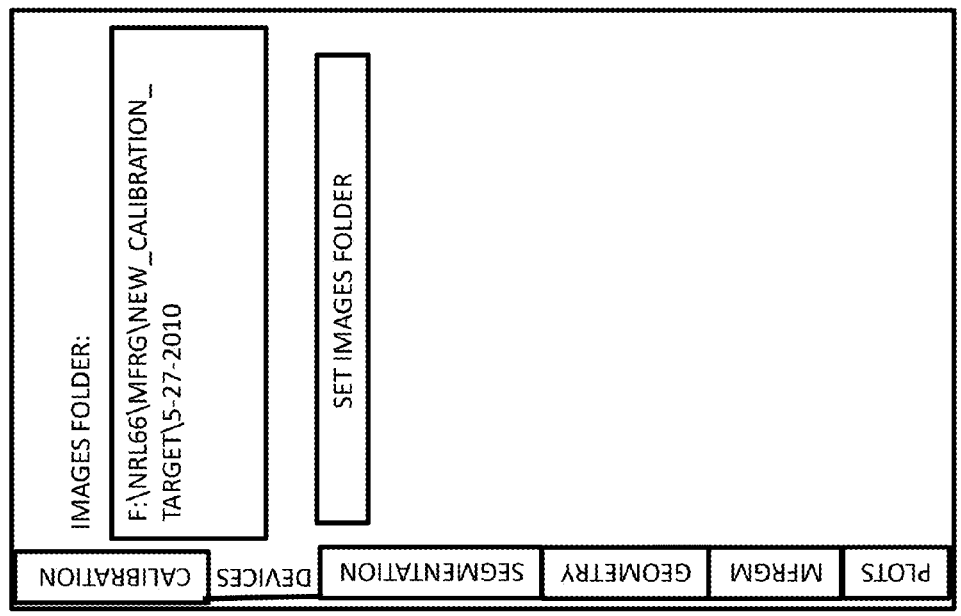
FIG. 8 illustrates the graphical user interface devices widget that allows users to select the imaging device in use.

FIG. 8 illustrates the devices widget. The devices tab on the graphical user interface screen used to select the imaging device that will transmit images to the ReMDiS-3D. Examples include a stored file of images, or streams of images as they are captured by different types of cameras.

Figure 9:
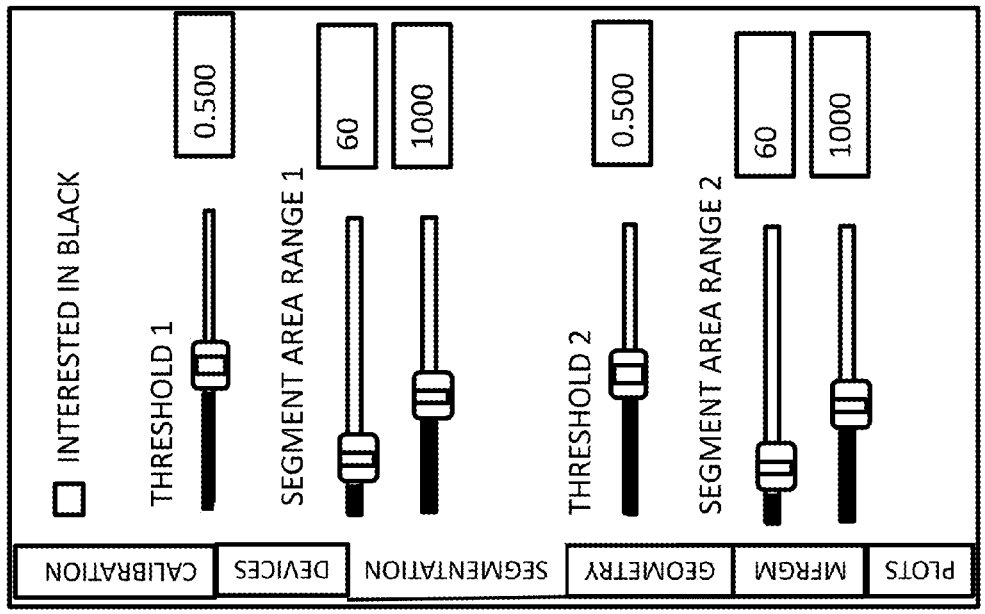
FIG. 9 shows the graphical user interface segmentation widget.

FIG. 9 shows the segmentation widget. The segmentation tab on the graphical user interface screen opens the segmentation widget, which allows the user to select the feature detection parameters. Those include filters that operate on the gray scale intensity and area of detected features. The gray scale filter ranges from 0 to 1, where 0 represents either black or white (and versa for 1), depending on whether an "Interested in black" check box is checked. The segmentation ranges represent square pixels.

Figure 10:
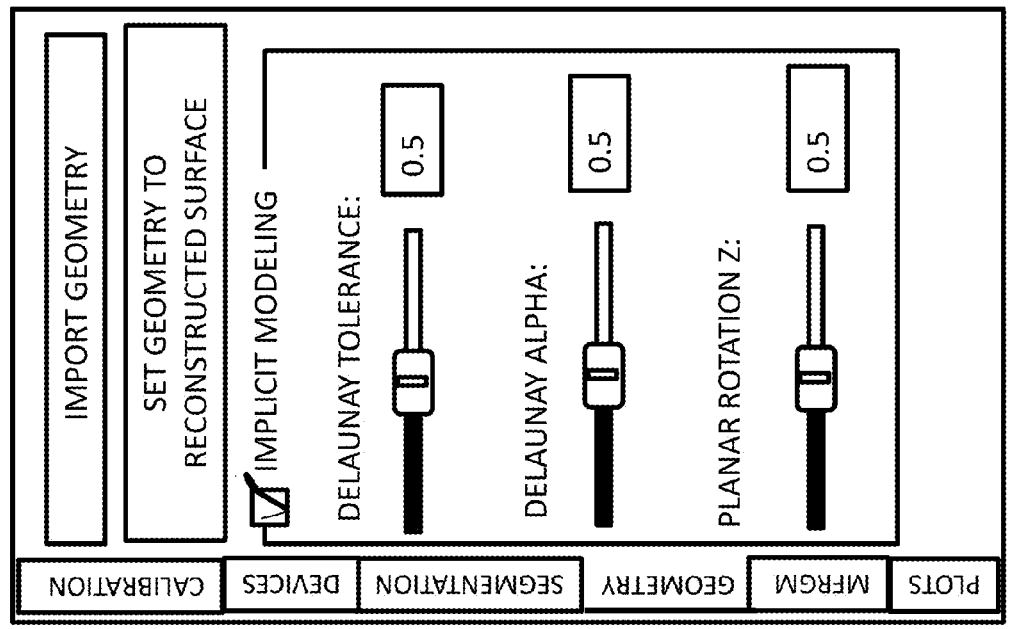
FIG. 10 shows the graphical user interface geometry widget.

FIG. 10 shows the geometry widget. The geometry tab on the graphical user interface screen opens the geometry widget, which allows the user to select between different options for the geometric properties of the results domain. By default ReMDiS-3D operates on the same set of nodes as this of the centroids of the features on the image. However, by importing another set of points, the user can set the values of the field variables at user-predefined points. Reverting back to the default can be done with a "Set geometry to reconstructed surface" push button on the graphical user interface screen.

The Delaunay tolerance and the Delaunay alpha values are used to define the algorithm that detects the underlying geometry by making certain assumptions on the local density of the features detected on the image. The Delaunay alpha value defines the minimum distance below which ReMDiS-3D will regard two points "disconnected" hence defining an opening in the geometry. By properly choosing a dense enough grid when the specimen is marked, this facility can help into almost automated geometry identification. The quantities in the Delaunay options are in the calibration points unit. Finally, the planar rotation z (measured in degrees) defines an additional option to rotate the coordinate system relative to the out of plane axis and serves misalignment correction purposes.

Figure 11:
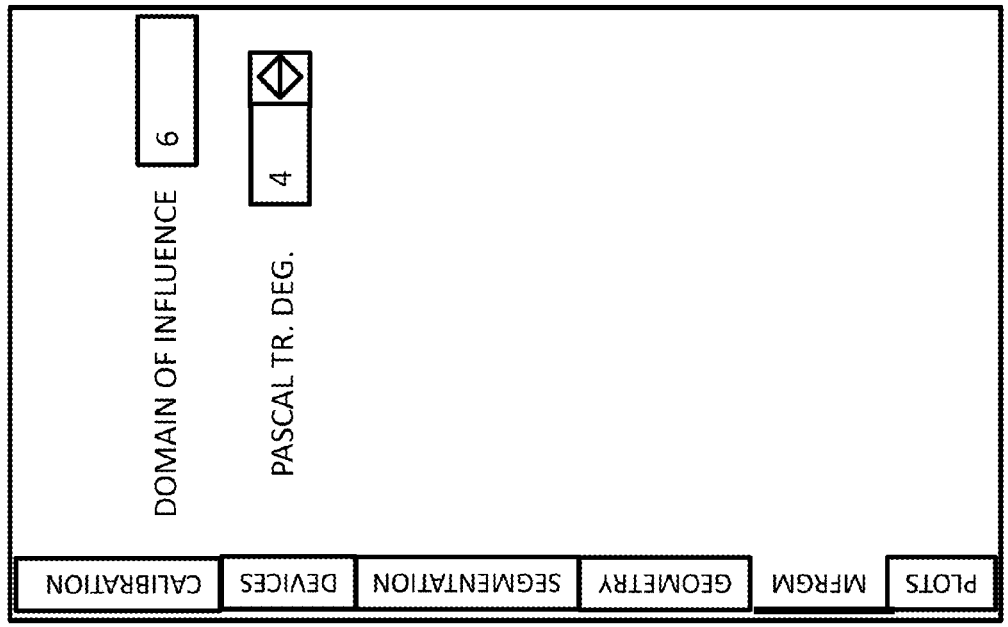
FIG. 11 shows the graphical user interface Mesh Free Random Grid (MRG) Method widget.

FIG. 11 shows the Mesh Free Random Grid (MRG) Method widget. The MRG tab on the graphical user interface screen opens the MRG widget, which allows the user to select the Mesh Free Random Grid Method options, including the Domain of influence and the Pascal Triangle shape function polynomial degree. The Domain of influence is in the calibration object units. A good value for the domain of influence is approximately two to four times the mean dot distance. A good value for the Pascal Triangle Polynomial is a degree of between 4 and 12, and preferably between 4 and 6.

Figure 12:
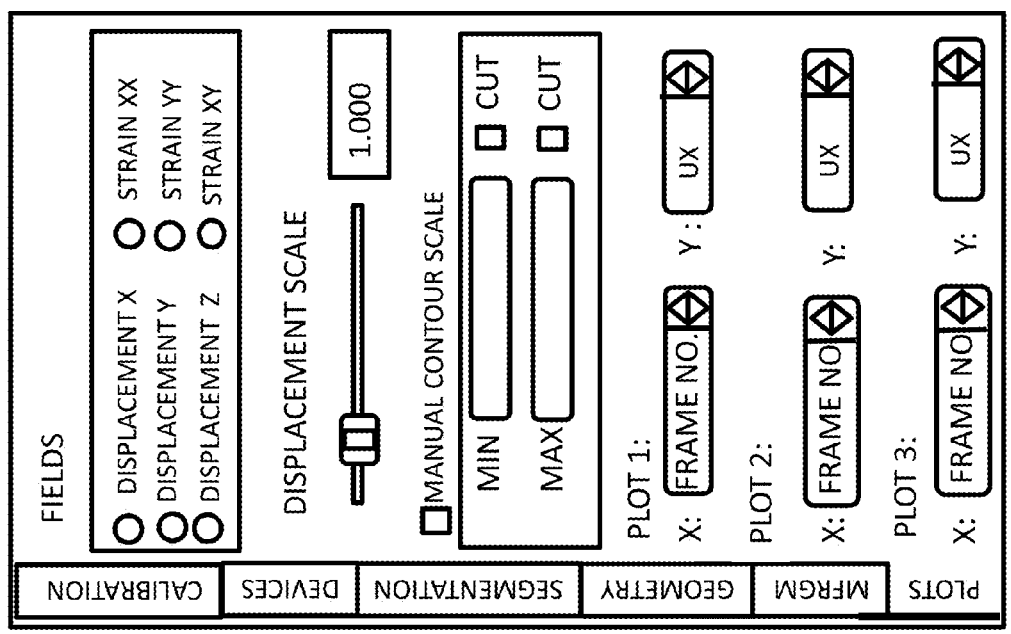
FIG. 12 shows the graphical user interface Plot widget.

FIG. 12 shows the Plot widget, selected using the Plot widget tab on the graphical user interface screen. The results options can be chosen for either the 3D view or each of the 2D plots. For the 3D view it is possible to choose between the following field variables: displacement along the x axis, displacement along the y axis, displacement along the z axis, and the three surface strains: Strain xx ($\epsilon_{xx}$), Strain yy ($\epsilon_{yy}$), and Strain xy ($\epsilon_{xy}$).

It is also possible to choose between automatic or manual color ranges for the display of the full field variables. To enable this function the user must check the "Manual contour scale" option and input the appropriate minimum and maximum values for the field variables. Normally the upper and lower values function as color-saturated limits By checking the "cut" checkbox the saturation option is disabled and any region with a field variable value outside the limit range is not displayed.

An exemplary ReMDiS-3D system example currently supports two modes for the 2D plots, in which the field variables can be plotted either versus the frame number or versus one of the predefined quantities stored in the data files. The predefined quantities stored in the data files can be defined for different test machines, including for example, the six degree of freedom hexapod test machine described in U.S. patent application Ser. No. 13/400,170, incorporated by reference herein.

Figure 13A:
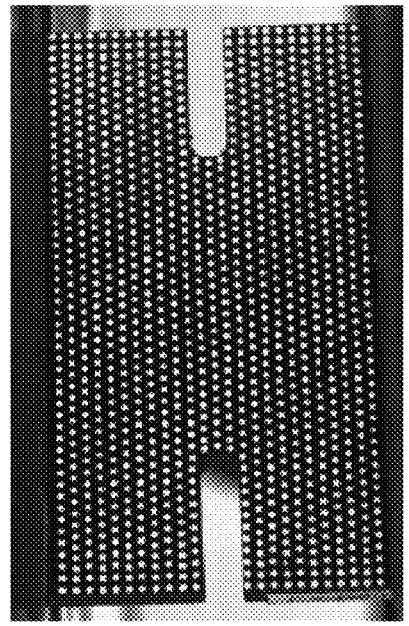
FIGS. 13A and 13B illustrate a stereoscopic image pair of the test specimen taken with two imaging devices.
Figure 13B:
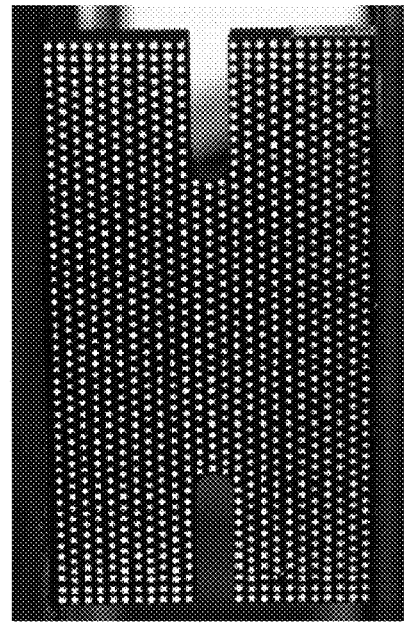

ReMDiS-3D results for a combined tension-out of plane experiment are shown in FIG. 14A-14I. The specimen under test was a composite specimen manufactured from AS4/3501-6 carbon/epoxy uni-directional prepreg, with nominal ply thickness of 0.14 mm FIGS. 13A and 13B illustrate a stereoscopic image pair of the test specimen at 1600×1200×16 bit resolution.

The specimen was subjected to tension and out of plane displacement up to fracture. The terminal tension load was 14150 kN, and during the test, approximately 400 stereo frames were captured. The processing speed for the 2×1600×1200×16-bit stereo frames was about 4 frames per second, including calculation of strain and visualization of the results, on an Intel i7-975x based Ubuntu system, running on 2 of its 4 cores.

In FIG. 14A-14I, nine images are shown, showing the three strain components $\epsilon_{xx}$ (vertical), $\epsilon_{yy}$ (horizontal) and $\epsilon_{xy}$ (shear), for three different tensile loads (4207 kN, 12018 kN and 13639 kN): 14A [$\epsilon_{xx}$ at tensile load=4207 kN]; 14B [$\epsilon_{yy}$ at tensile load=4207 kN]; 14C [$\epsilon_{xy}$ at tensile load=4207 kN]; 14D [$\epsilon_{xx}$ tensile load=12018 kN]; 14E [$\epsilon_{yy}$ a t tensile load=12018 kN]; 14F [$\epsilon_{xy}$ at tensile load=12018 kN]; 14G [$\epsilon_{xx}$ tensile load=13639 kN]; 14H [$\epsilon_{yy}$ at tensile load=13639 kN]; and 14I [$\epsilon_{xy}$ at tensile load=13639 kN]. Note that the amount of strain is illustrated by a change in color, with red being the highest strain, and blue being the lowest strain.

Figure 14A:
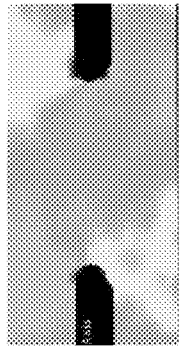
FIG. 14A-14I show the results from the mesh-free random grid analysis of data from two cameras using the ReMDiS-3D workbench for a combined tension and out of plane material test.
Figure 14B:
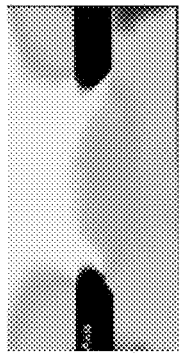
Figure 14C:
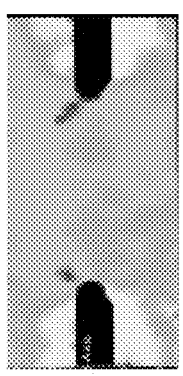
Figure 14D:
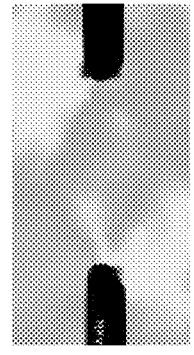
Figure 14E:
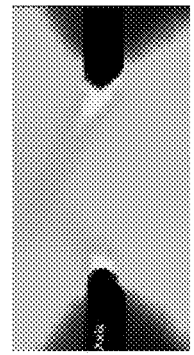
Figure 14F:
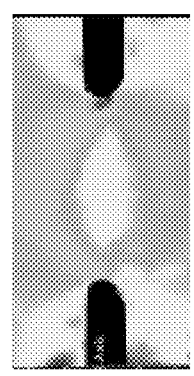
Figure 14G:
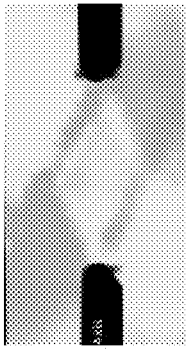
Figure 14H:
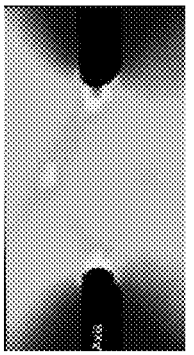
Figure 14I:
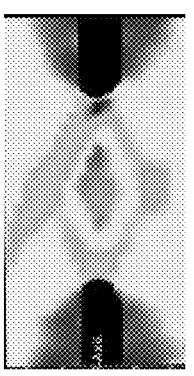

Only the results in FIGS. 14A, 14B, and 14C (tensile load=4207 kN) are within the linear region of the material, while the results for tensile load equal to 13693 kN are very close to the onset of cracks.

FIGS. 15A and 15B compare the $\epsilon_{yy}$ results for the specimen determined using the ReMDiS-3D software to a finite-element-analysis numerical model of the same specimen, showing good agreement.

As described above, the ReMDiS-3D software application implements a workbench for the mesh-free random grid material analysis method in three dimensions, allowing full field analysis and display of displacement and strain on a three dimensional (non-planar) surface.

The system can include both a deformable body or test specimen, visually patterned in the manner described above, a test device for deforming the body, the image acquisition system, data storage for storing the images and associated information, communications links for transmitting the images and associated information to the computer system that implements the processing steps (including the point or pattern matching algorithms, and algorithms for calculating and displaying the full field).

Portions of the system operate in a computing operating environment, for example, a desktop computer, a laptop computer, a mobile computer, a server computer, and the like, in which embodiments of the invention may be practiced. A brief, general description of a suitable computing environment in which embodiments of the invention may be implemented. While the invention will be described in the general context of program modules that execute in conjunction with program modules that run on an operating system on a personal computer, those skilled in the art will recognize that the invention may also be implemented in combination with other types of computer systems and program modules.

Generally, program modules include routines, programs, components, data structures, and other types of structures that perform particular tasks or implement particular abstract data types. Moreover, those skilled in the art will appreciate that the invention may be practiced with other computer system configurations, including hand-held devices, multiprocessor systems, microprocessor-based or programmable consumer electronics, minicomputers, mainframe computers, and the like. The invention may also be practiced in distributed computing environments where tasks are performed by remote processing devices that are linked through a communications network. In a distributed computing environment, program modules may be located in both local and remote memory storage devices.

An illustrative operating environment for embodiments of the invention will be described. A computer comprises a general purpose desktop, laptop, handheld, mobile or other type of computer (computing device) capable of executing one or more application programs. The computer includes at least one central processing unit ("CPU"), a system memory, including a random access memory ("RAM") and a read-only memory ("ROM"), and a system bus that couples the memory to the CPU. A basic input/output system containing the basic routines that help to transfer information between elements within the computer, such as during startup, is stored in the ROM. The computer further includes a mass storage device for storing an operating system, application programs, and other program modules.

The mass storage device is connected to the CPU through a mass storage controller (not shown) connected to the bus. The mass storage device and its associated computer-readable media provide non-volatile storage for the computer. Although the description of computer-readable media contained herein refers to a mass storage device, such as a hard disk or CD-ROM drive, it should be appreciated by those skilled in the art that computer-readable media can be any available media that can be accessed or utilized by the computer.

By way of example, and not limitation, computer-readable media may comprise computer storage media and communication media. Computer storage media includes volatile and non-volatile, removable and non-removable media implemented in any method or technology for storage of information such as computer-readable instructions, data structures, program modules or other data. Computer storage media includes, but is not limited to, RAM, ROM, EPROM, EEPROM, flash memory or other solid state memory technology, CD-ROM, digital versatile disks ("DVD"), or other optical storage, magnetic cassettes, magnetic tape, magnetic disk storage or other magnetic storage devices, or any other medium which can be used to store the desired information and which can be accessed by the computer.

According to one embodiment, the computational workbench for visualizing the full field characteristics of deformable bodies may include a number of program modules.

According to various embodiments of the invention, the computer may operate in a networked environment using logical connections to remote computers through a network, such as a local network, the Internet, etc. for example. The computer may connect to the network through a network interface unit connected to the bus. It should be appreciated that the network interface unit may also be utilized to connect to other types of networks and remote computing systems. The computer may also include an input/output controller for receiving and processing input from a number of other devices, including a keyboard, mouse, etc. (not shown). Similarly, an input/output controller may provide output to a display screen, a printer, or other type of output device.

As mentioned briefly above, a number of program modules and data files may be stored in the mass storage device and RAM of the computer, including an operating system suitable for controlling the operation of a networked personal computer. The mass storage device and RAM may also store one or more program modules. In particular, the mass storage device and the RAM may store application programs, such as a software application, for example, a word processing application, a spreadsheet application, a slide presentation application, a database application, etc.

It should be appreciated that various embodiments of the present invention may be implemented as a sequence of computer implemented acts or program modules running on a computing system and/or as interconnected machine logic circuits or circuit modules within the computing system. The implementation is a matter of choice dependent on the performance requirements of the computing system implementing the invention. Accordingly, logical operations including related algorithms can be referred to variously as operations, structural devices, acts or modules. It will be recognized by one skilled in the art that these operations, structural devices, acts and modules may be implemented in software, firmware, special purpose digital logic, and any combination thereof without deviating from the spirit and scope of the present invention as described herein.

What is claimed as new and desired to be protected by Letters Patent of the United States is:

1. A computer-implemented method for measuring full field deformation characteristics in three dimensions of a deformable body upon which a visible dot pattern has been applied, the method comprising:
    (a) receiving corresponding sequences of images from at least two imaging devices positioned facing the dot pattern at different angles, of images including a first frame taken before deformation of the body and a second frame taken after deformation of the body, of the dot pattern before and after deformation of the body;
    (b) for each image in the first frame, identifying the centroids of the dots with a computer processor, matching the centroids of the dots in an image from one imaging device to the centroids of the dots in a corresponding image from the other imaging device, and generating a three dimensional representation of the centroids of the pattern of dots from the two images;
    (c) repeat (b) for both images in the second frame;
    (d) matching the three dimensional representation of the centroids in the first frame to the three dimensional representation of the centroids in the second frame;
    (e) calculating the displacement vector of the centroids between the first frame and the second frame; and
    (f) calculating full field displacement in three dimensions based on the displacement vector of the centroids.

2. The method as in claim 1, further comprising:
calculating a full field strain tensor based on the calculated displacement.

3. The method as in claim 1, wherein said receiving corresponding sequences of images includes digitally photographing the side of the deformable body during deformation with two or more digital video cameras or still imaging cameras.

4. The method as in claim 1, wherein said identifying the centroids of the dots includes light integration of the image to find the centroid of each dot.

5. The method as in claim 1, further comprising eliminating irregular objects from both images in a frame.

6. The method as in claim 5, wherein said eliminating irregular objects includes eliminating objects with a dot intensity below a threshold value, objects with a pixel area outside a predetermined range, or objects with an out-of-range aspect ratio, an out-of-range moment of inertia, an out-of-range major axes direction, or an out-of-range compactness ratio.

7. The method as in claim 1, further comprising:
receiving performance characteristics from a user, and selecting mesh free approximation parameters based on the performance characteristics.

8. The method as in claim 7, further comprising:
displaying and storing the acquired images, user input, and calculated displacement and strain component, wherein said displacement and strain components are graphically shown using a color scale.

9. The method as in claim 1, further comprising:
displaying a plot of displacement, elongation, or strain versus time or image frames.

10. The method as in claim 1, wherein at least one of the dot size, shape, or spacing is not uniform.

11. The method according to claim 1, wherein said generating a three dimensional representation of the centroids of the pattern of dots from the two images comprises:
    for each of the dots in the pattern, triangulating a three dimensional position of the centroid of the dot from a position of the centroid of the dot in the image from the imaging device, a position of the centroid of the dot in the corresponding image from the other imaging device, and projection matrices of both imaging devices;
    such that the three dimensional representation of the centroids of the pattern of dots is a set of all of the triangulated three dimensional positions of the centroids.

12. An apparatus for measuring full field deformation characteristics of a deformable body having a pattern of optically distinct marks disposed on a surface of the body, the apparatus comprising:
    at least two cameras arranged facing the pattern of optically distinct marks at different angles to the surface of the deformable body for acquiring corresponding sequences of images of the pattern of marks before and after deformation of the deformable body; and
    a computer processor having programmed instructions thereon for identifying the centroids of each image, matching the centroids between corresponding images in a frame from each of the cameras, generating a three-dimensional representation of the centroids in a frame based on the two corresponding images in that frame, calculating the displacement vector of the centroids of the three dimensional representation and a later three dimensional representation of the centroids, and calculating full field displacement fields and strain tensor based on the displacement vector of the centroids.

13. The system according to claim 12, wherein the full field displacement fields and strain tensor are calculated using a mesh free approximation.

14. The system as in claim 12, the processor having further instructions for identifying the centroids of the dots includes light integration of the image to find the centroid of each dot.

15. The system as in claim 12, the processor having further instructions for eliminating irregular objects from both images in plurality of frames in the sequences of images based on objects having a intensity below a threshold value of intensity, a pixel area outside a predetermined range, an out-of-range aspect ratio, an out-of-range moment of inertia, an out-of-range major axes direction, or an out-of-range compactness ratio.

16. The system as in claim 12, the processor having instructions for a graphical user interface for receiving performance characteristics from a user, and selecting mesh free approximation parameters based on the performance characteristics.

17. The system as in claim 12, further comprising: a display connected to the processor, and the processor having further instructions for displaying and storing the acquired images, user input, and calculated displacement and strain component, wherein said three dimensional displacement and strain field components are graphically shown using a color scale.

* * * * *